United States Patent
Yaccarino, III et al.

(10) Patent No.: US 7,044,968 B1
(45) Date of Patent: May 16, 2006

(54) COMPOUND BONE STRUCTURE OF ALLOGRAFT TISSUE WITH THREADED FASTENERS

(75) Inventors: Joseph A. Yaccarino, III, Somerset, NJ (US); Arthur A. Gertzman, Stony Point, NY (US); Raymond G. Ferrara, Branchburg, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 941 days.

(21) Appl. No.: 09/503,166

(22) Filed: Feb. 14, 2000

Related U.S. Application Data (63) Continuation-in-part of application No. 09/196,251, filed on Nov. 20, 1998, now Pat. No. 6,025,538.

(51) Int. Cl.
*A61F 2/28* (2006.01)
*A61F 2/44* (2006.01)

(52) U.S. Cl. .................. 623/16.11; 623/17.11
(58) Field of Classification Search ............. 623/16.11, 623/17.11, 17.12, 17.13, 17.14, 17.15, 17.16
See application file for complete search history.

(56) References Cited

U.S. PATENT DOCUMENTS

| | | | |
|---|---|---|---|
| 4,858,603 A | 8/1989 | Clemow et al. | |
| 4,877,020 A | 10/1989 | Vich | |
| 4,932,973 A | 6/1990 | Gendler | |
| 5,112,354 A | 5/1992 | Sires | |
| 5,571,190 A * | 11/1996 | Ulrich et al. | 623/17 |
| 5,899,939 A * | 5/1999 | Boyce et al. | 623/16 |
| 5,968,047 A * | 10/1999 | Reed | 606/76 |
| 6,200,347 B1 | 3/2001 | Anderson et al. | |
| 6,258,125 B1 * | 7/2001 | Paul et al. | 623/17.11 |

OTHER PUBLICATIONS

Albee, The Improved Albee Bone Mill, American Journal of Surgery, Mar. 1938, No. 3 ps 657-60.
Albee, Bone Graft Surgery in Disease Injury and Deformity, 1940, Ch. I pp. 22,23,30 D. Appleton Century Company.

* cited by examiner

*Primary Examiner*—Corrine McDermott
*Assistant Examiner*—Hieu Phan
(74) *Attorney, Agent, or Firm*—Gipple & Hale; John S. Hale (57) ABSTRACT

A composite allograft bone device having a first bone member body with a face that defines a plurality of spaced projections forming a pattern and a second bone member body defining a face that forms a plurality of spaced projections forming a second pattern. The projections in the first face allow the two bodies to be mated together. The mated bodies form a composite bone device which is provided with a throughgoing bore and a threaded rod member mounted in the throughgoing bore extending into and engaging the bone member bodies holding the same together. Alternatively a rod member with a demineralized or knurled outer surface can be press fit into the throughgoing bore engaging the bone member bodies in an interference fit holding the same together. In another embodiment an inner central cancellous bone block is surrounded by plates or a U shaped base constructed of cortical bone material.

1 Claim, 5 Drawing Sheets

COMPOUND BONE STRUCTURE OF ALLOGRAFT TISSUE WITH THREADED FASTENERS

RELATED APPLICATIONS

This is a continuation-in-part of U.S. patent application Ser. No. 09/196,251 filed Nov. 20, 1998 and issued into U.S. Pat. No. No. 6,025,538 on Feb. 15, 2000.

BACKGROUND OF THE INVENTION

1. Field of Invention

The present invention generally relates to allograft bone devices for surgical implantation into bone tissue and particularly to a composite allograft bone device constructed from two or more separate bone pieces made from allograft, autograft and xenograft bone tissue that can be fastened together to have dimensions that are larger than the dimensions of naturally occurring bone suitable for implantation in a surgical site.

2. Description of the Prior Art

Allograft bone tissue is widely used in orthopedic, neuro-, maxillofacial, podiatric and dental surgery. Allograft tissue is valuable in these fields of surgery because it is strong and it biointegrates well over time with the recipient patient's tissue. Allograft bone tissue can be shaped for specific surgical applications by the surgeon or by a bone product manufacturer in a manufacturing environment before the allograft bone tissue is transferred to the surgeon. Unfortunately because of the size limitation of the bone material only devices of a certain size could be constructed.

Surgical implants constructed entirely from allograft bone tissue are generally superior to implants constructed from synthetic or nonabsorbable polymers or metals because allograft bone tissue is bioinert and integrates well with the surrounding tissues.

Allograft bone occurs in two basic forms: 1) cancellous bone (also referred to as trabecular bone) and 2) cortical bone. Cortical bone is highly dense and has a compound structure comprised of calcium hydroxyapatite reinforced with collagen fiber. This cortical bone material is the predominant load bearing component of long bones in the human body. Many shapes and forms can be fabricated from allograft cortical bone tissue including rods, screws, plates, intervertebral discs and the like for use in human surgery. Cortical bone has one serious limitation that plastics and metal do not have. Bone parts and bone products made from allograft cortical tissue are limited in size, dimension and shape because of the anatomical limits on the thickness and length of the source bone.

As an example, the largest long bone, the femur bone, has a thick cortical wall that varies in thickness from about two millimeters to about ten millimeters. The majority of the femoral cortical bone wall typically ranges from about three millimeter to about eight millimeters in thickness. The length of the cortical tissue is also naturally limited by the size and the weight of the allograft tissue donor. Accordingly, specific implants fabricated from cortical bone have previously not been larger than these natural anatomical dimensions. The other long bones of the human body, the humerous, the tibia, the fibula, the radius, the ulna, the ribs, etc., are similarly limited in dimension. Shaped implants made from these other long bones are also necessarily limited in dimension.

The dimensional limit that has been achieved with single piece cortical bone is about 10 mm×about 13 mm cross-sections. The length of these sections can be much longer as they are taken from the long axis of the bone. The research that has been completed shows femoral sections ranging from 3 mm×4 mm to 10 mm×10 mm at the mid-shaft and tibial sections 3 mm×6 mm to 10 mm×13 mm at the proximal end.

Many medical problems and surgical procedures require implants larger than have previously been made out of allograft cortical tissue. It is desirable to have a surgical implant made entirely out of allograft cortical tissue that is larger than can be made from a single piece of naturally occurring bone. Two requirements must be met by any implant fabricated entirely from cortical bone, however, to achieve a successful surgical result. First, the components must be held together in such a way that the mechanical structure of the implant is not compromised during the surgical implantation procedure. Many surgical implants are implanted in the recipient patient with a large applied force as they are actually hammered in as is the case for an intervertebral implant. Second, the compound structure of the implant must hold together during the post-operative period during which the allograft tissue is resorbed and remodeled.

The prior art contains many references directed to fasteners, spinal cages and devices which are constructed of inert metals or plastics which are used in bone repair. There are relatively few devices used in bone repair constructed of allograft bone because of the difficulty in obtaining and shaping the material and the natural limits placed on the size of the device based on the constraints of the sizes of the natural bone which can be shaped to form devices of a larger required size.

One example of an allograft device is disclosed in U.S. Pat. No. 4,877,020 which shows a dowel made of bone having a helicoidal thread. Other fasterner made of allograft bone such as screws, pins, anchors, plates and the like are disclosed in U.S. Pat. No. 5,968,047.

Another device is shown in U.S. Pat. No. 4,932,973 where the use of a perforated bone matrix for use in insertion or implantation in a bone mass to promote bone growth is disclosed.

Similarly U.S. Pat. No. 5,112,354 discloses the preparation of an allograft bone segment for use in skeletal reconstruction. The bone segment is demineralized and a multiplicity of bores (described as pores) are drilled into the bone mass in a pattern to maximize the surface area of the implant. Some of the bores are drilled through the bone mass at the center of the hexagon pattern.

U.S. Pat. No. 5,439,684 is directed toward various swollen demineralized bone constructions such as sleeves, rectangular pledgets and wedges. The pledgets and wedges can be used as invertebrate support blocks. The bone can be machined into a desired shape for implantation such as a sheet, disc, ring, cube, cylinder or sliced and wrapped into a tubular shape. However, all of these bone structures are limited to the size and shape of the original material.

Another patent of interest is U.S. Pat. No. 4,858,603 which shows a bone rod which is placed through an angular bore cut through two separate pieces of bone to hold the pieces together in a fixed secured relationship. The bone rod is made from a polymer which is absorbable in an animal body.

Until now, the only way that separate bone pieces could be joined together to arrive at a larger device has been to tongue and groove the respective pieces which creates shearing areas and limits the use to which such constructed device could be used. This is a significant problem where a device is placed under stress and shearing forces as for example where it is hammered into place between vertebrae or into other bone areas. The first disclosure of joining together separate pieces of allograft bone is believed to be set forth in various articles by F. Albee. This disclosure also shows the machining of dowels, rods and screws from bone. F. Albee, *Bone Graft Surgery in Disease, Injury and Deformity* p. 22 (1940); and F. Albee, *The Improved Albee Bone Mill*, American Journal of Surgery p. 657 (March 1938).

Accordingly, there is a need for implantable shaped structures made entirely out of cortical bone tissue that are larger than naturally occurring bone structures and are made out of cortical tissue. There is also a need for larger shaped bone structures made out of a combined cortical/cancellous structure.

SUMMARY OF THE INVENTION

The present invention is directed toward a shaped structure made out of allograft bone tissue that is larger than the natural dimensions of a cortical bone layer made by combining two or more smaller pieces of bone to form a compound bone structure.

The preferred compound bone structure is comprised of a first bone member having a first mating face constructed and arranged to support a load applied in a direction that is normal to the first mating face and to receive and engage a complimentary mating face of a second bone member. The second mating face is constructed and arranged to support a load applied in the direction normal to the second mating face and to engage the first mating face: so that the first and second bone members cooperate to form the compound bone structure.

The compound bone structure has an exterior surface that can be shaped to form an implant that can support the anatomical load and orient the implant in the surgical site so that the anatomical load is applied to the engaged first and second mating faces in the normal direction. Complimentary mating structures formed on the first and second mating faces prevent displacement of the first bone member with respect to the second bone member in both a longitudinal direction and a transverse direction when an anatomical load is applied.

At least one fastener either threaded or of an interference fit is placed through the component bone members of compound bone structure extending through the compound bone structure and across the mating faces of the bone members.

It is an object of the invention to make a compound bone structure from bone tissue of smaller bone segments for use in implantation into a surgical site and to support an anatomical load applied to the compound bone structure during a post-operative period while the implanted bone tissue is resorbed and remodeled.

It is another object of the invention to fabricate shapes out of allograft cortical tissue that would enable larger parts to be made out of cortical tissue.

It is still another object of the invention to fabricate shapes out of composite allograft cortical and cancellous tissue that would enable a larger structure to be made out of composite parts.

It is still another object to use partially demineralized bone rods in an interference fit in a bore formed in the composite bone structure to hold the same together and promote bone growth.

It is yet another object of the invention to form a compound bone structure which is implantable and is larger than bone pieces that are found in nature.

These and other objects, advantages, and novel features of the present invention will become apparent when considered with the teachings contained in the detailed disclosure along with the accompanying drawings.

DETAILED DESCRIPTION OF THE PREFERRED EMBODIMENT

Figure 1:
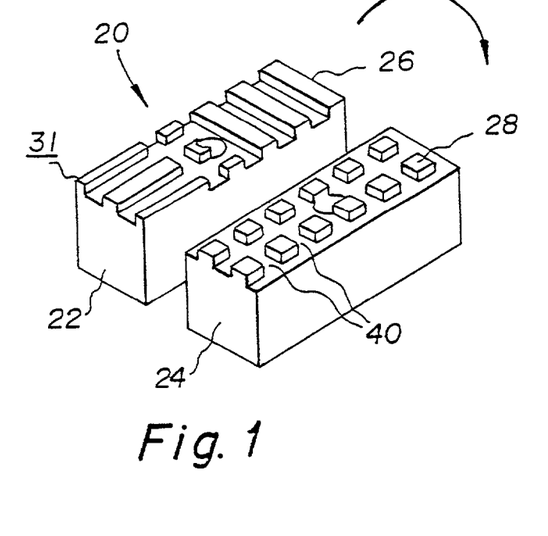
FIG. 1 shows an exploded flipped perspective elevational view of the inventive compound bone device without a mechanical fastener.
Figure 2:
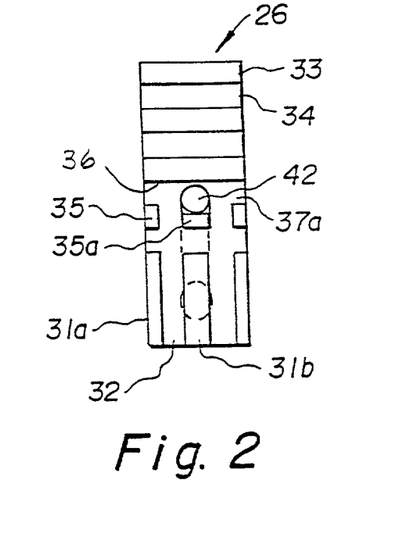
FIG. 2 shows a top plan view of one of the bone members of the inventive compound bone device shown in FIG. 1.
Figure 3:
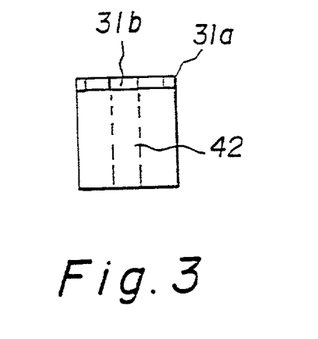
FIG. 3 shows an end elevational view of the bone member shown in FIG. 2 with the bore shown in phantom.
Figure 4:
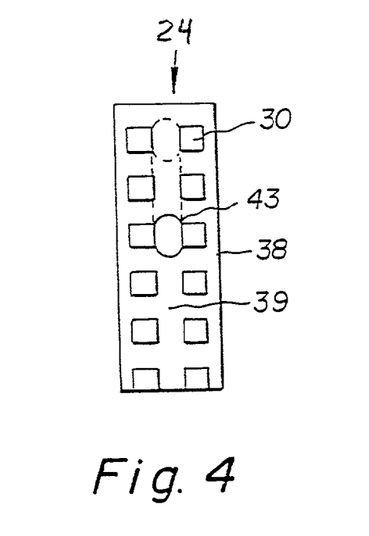
FIG. 4 shows a top plan view of a second member of the inventive compound bone device shown in FIG. 1.
Figure 5:
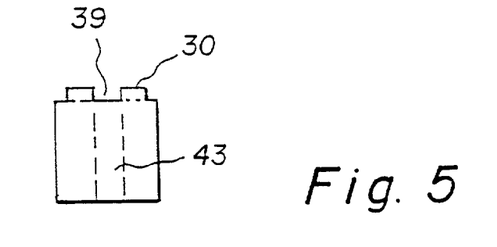
FIG. 5 shows an end elevational view of the bone member shown in FIG. 4 with the bore shown in phantom.
Figure 6:
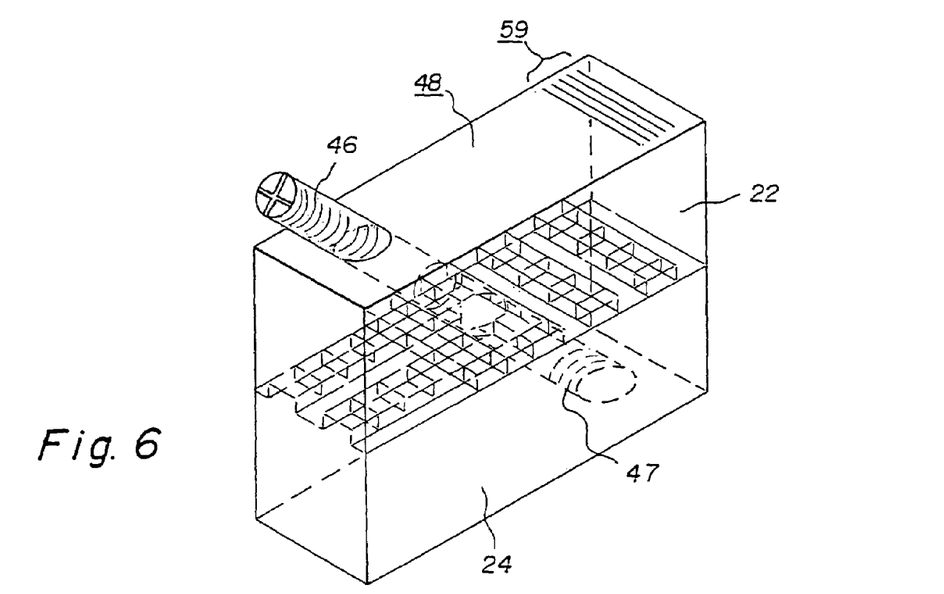
FIG. 6 shows an assembled perspective elevational view of the inventive compound bone device with the respective mating faces in phantom and a threaded rod being inserted.
Figure 7:
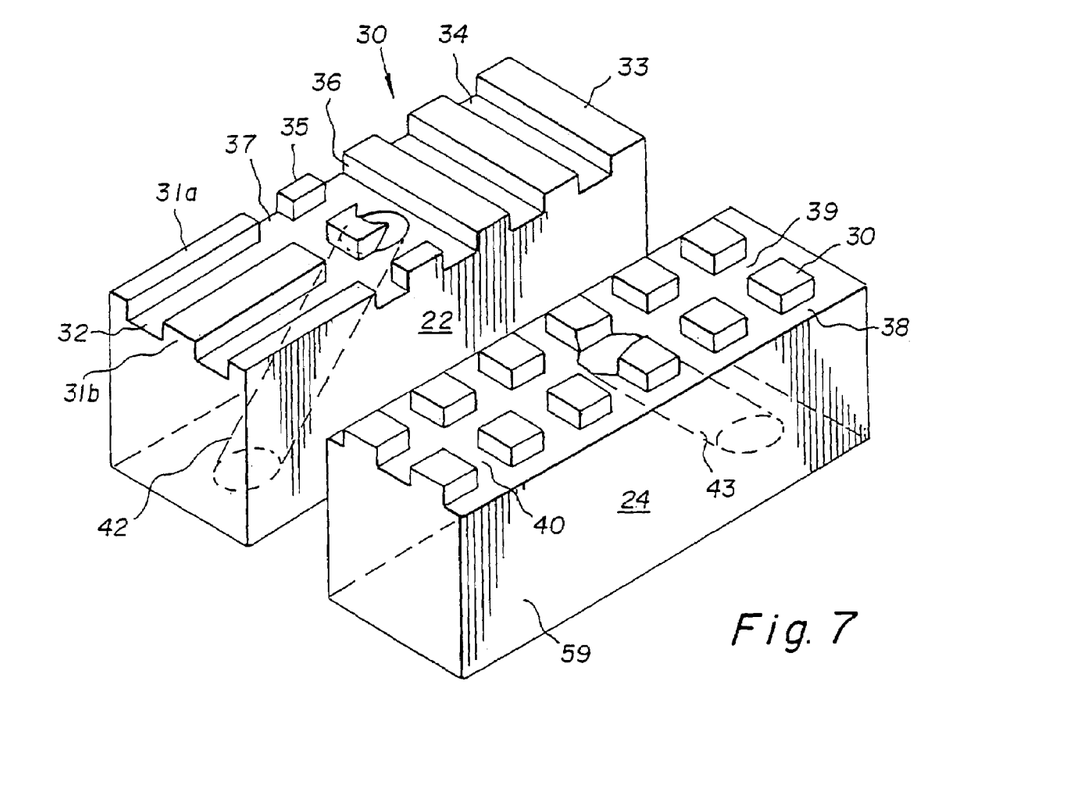
FIG. 7 shows an exploded flipped perspective view of the inventive compound bone device with rod removed and the rod bore in phantom.

The preferred embodiment and the best mode of the invention is shown in FIGS. 1–7. FIG. 1 shows an exploded side view of a compound bone device 20 with a first bone member 22 and a second bone member 24 flipped for viewing. The first and second bone members 22, 24 are constructed from rectangular blocks of bone tissue that have been machined or shaped by other suitable means. Each bone member 22, 24 has a mating face or engagement surface 26 and 28 as shown in FIGS. 2 and 4 respectively that has been shaped to form integral mating projections or teeth 30 on each face 26, 28 so that the members 22, 24 can be engaged to form the compound bone device 20 shown in FIG. 6.

Bone member 22 has a mating face 26 constructed with three bar projections 31 separated by grooves 32 formed on one end. The bar projections 31 run parallel to the longitudinal axis of the bar member and extend along the mating face less than ½ the length of the bar member. The grooves 32 are preferably around 2 to 2.12 mm in width and the side bars 31(a) have a width which is less than the width of the center bar 31(b). The other end of the bone member 22 has three bar projections 33 separated by grooves 34 running transverse the longitudinal axis and extending across the width of the bone member 22. The midsection of the bone member has a plurality of rectangular projections 35 formed by extending grooves 32 up to the side wall 36 of the inner transverse bar 33. The rectangular projections 35 are separated from the axially aligned bar members 31 by a groove 37 and the side wall 36 of inner transverse bar 33 by groove 37(a). The bars 31(b), 33 and center rectangular projection 35(a) have a width of approximately 2 mm.

Bone member 24 is formed with grooves 38 along each longitudinal side of the body and is also provided with a central groove 39 extending longitudinally the length of the bone member 24. Grooves 40 run across the width and transversely intersect grooves 38 and 39 forming projections 30. The grooves 38 located on opposite sides of the bone member 24 receive the side bars 31(a) and the side rectangular projections 35.

The mating projections or teeth range from 0.5 to 2.0 mm in height, preferably 1.0 mm and are formed by cutting a plurality of slots, grooves or channels ranging from 1 to 4 mm in width with a generally rectangularly shaped cross sections in each mating surface 26, 28 of the bone members. The channels or grooves 38–40 are of equal width dimensions and preferably have a width ranging from 2.0 mm to 2.12 mm apart.

The mating projections 30 and the channels on the bone members 22, 24 form complimentary inverse patterns that allow the members 22, 24 to be engaged or meshed together by press fitting the patterns on the mating faces together. This engagement and relationship of the various projections prevents relative motion between the members 22, 24 in both the transverse and longitudinal directions to stabilize the compound bone device 20 during subsequent machining of the exterior surface of the device 20 and during or after implantation in a surgical site.

Two biased or angled bores 42 and 43, respectively, extend through each bone members 22, 24. The bores 42 and 43 are shown in phantom in FIGS. 6 and 7. The bores 42 and 43 are oriented so that when the members 22, 24 are engaged, the bores 42 and 43 are axially aligned to form a continuous first bore 47 through the compound bone device 20. A cylindrical threaded rod 46 shown in FIG. 6 preferably made of cortical bone tissue is press fit into the continuous bore 47 to prevent the separation of the members 22, 24. Thus, the mating surfaces 26, 28 of the bone members 22, 24 are secured together by at least one threaded rod 46 positioned at an angle to the plane of the engaged mating surfaces and extending substantially the full thickness of the compound bone device 20. In the preferred embodiment shown in FIGS. 1–7, the wall forming bore 47 is cylindrical and threaded and the threaded rod 46 is cylindrical. The threaded rod 46 has a diameter slightly less than the diameter of the bore 47 so that the rod is retained in the bore by the threads of the bore. If desired a suitable medical adhesive can be use to insure that the rod stays in the bore during insertion. The threaded rod 46 is preferably cut from cortical bone but resorbable synthetic rods or metal rods could be used. It is also appreciated that the rod could be threaded at each end 48 with a smooth center section or be in the form of a bolt 330 threaded at one end and being held in position with an appropriately sized nut 332. The nut 332 can be constructed of cortical bone, synthetic (resorbable material) or metal. Thus the fasteners can be threaded into the bone or be held in place with cap means (not shown) or standard type nuts 332. The outer surfaces of bone members 22, 24 can be countersunk around the bores 47 forming a stepped recess or well so that the outer shape of the graft is maintained as the head or nut is located in the well of the countersink.

Figure 11:
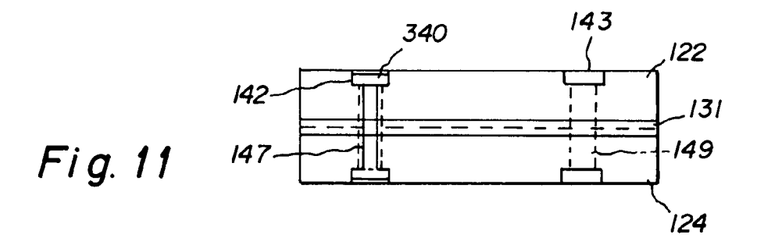
FIG. 11 is an assembled side elevational view of a compound bone structure with a countersunk rivet fastener member.

An alternate embodiment is also formed with a stepped countersink at one end of the bore on the outer surface of the respective bone members to hold rivets 340 made of resorbable synthetic material or metal.

Figure 12:
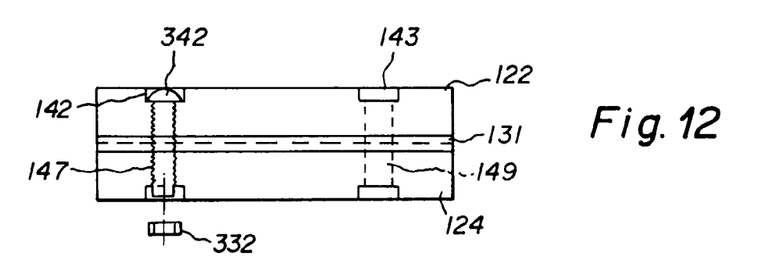
FIG. 12 is an assembled side elevational view of a compound bone structure with a countersunk screw fastener member.

It is also envisioned that the threaded rods could be replaced by screws 342 made from bone material or a resorbable synthetic.

Figure 8:
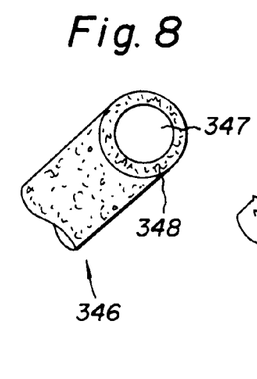
FIG. 8 shows an enlarged partial perspective view of a partially demineralized rod for insertion and interference fit in the bore of a compound bone device.

If desired the cortical rod 346 can be unthreaded with an outer demineralized surface layer 348 (which increases toughness and malleability) leaving an allograft bone core 347 present in the cortical rod 346 as shown in FIG. 8 and the same is press fit into bores that are slightly undersized from the diameter of the cortical rod 346.

Figure 8A:
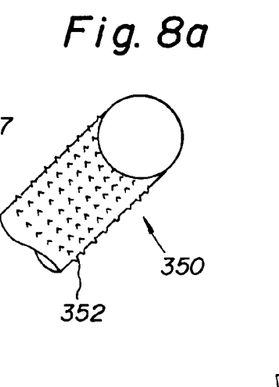
FIG. 8a shows an enlarged partial perspective view of a rod having a knurled outer surface for insertion and interference fit in the bore of a compound bone device.
Figure 8B:
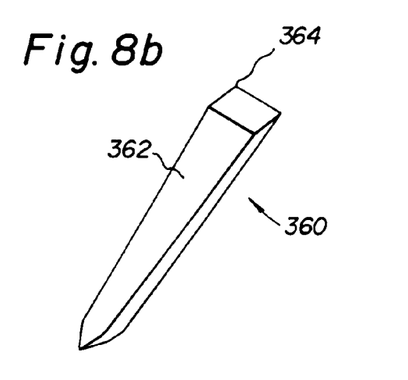
FIG. 8b shows an enlarged perspective view of a wedged nail for insertion and interference fit in the bore of a compound bone device.

A knurled rod 350 has a scored or knurled surface 352 as shown in FIG. 8a can also be used and the same is press fit into bores that are slightly undersized. It is also envisioned that the knurled rods could be made from cortical bone material or a resorbable synthetic. Likewise a wedge or wedge nail 360 having planar sides 362 with angular edges 364 as shown in FIG. 8b made from bone material or a resorbable synthetic and the same is press or interference fit into bores that are circular in cross section and are slightly undersized from length of the diagonals from the opposing edges of the square or rectangular cross section of the wedged nail. It will be appreciated that this greater size from the diameter of the bore must extend along a length of the wedge nail 360 so that both or multiple sections of the composite bone assembly are engaged.

It will be appreciated that three or more bone members can be fastened together by forming projections on both sides of the bone members. As an example, bone member 24 could be provided with an identical mating face on its opposite side which would engage another bone member shaped identical to bone member 22.

Figure 9:
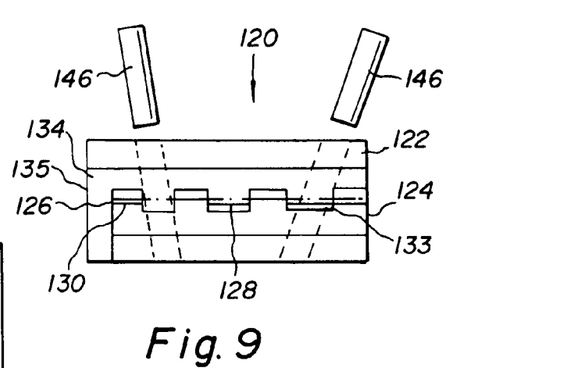
FIG. 9 is an assembled side elevational view of the compound bone device showing the threaded rods removed and rod bores in phantom.

FIG. 9 shows an alternative embodiment of the compound bone device 120 constructed with a first bone member 122 and a second bone member 124. The first and second bone members 122, 124 are constructed from rectangular blocks of bone tissue that has been machined or shaped by other suitable means. Each bone member 122, 124 has a mating face or surface 126 and 128 that has been shaped to form integral mating projections or teeth 130 on each face 126, 128 so that the members 122, 124 can be engaged to form the compound bone device 120.

Figure 9A:
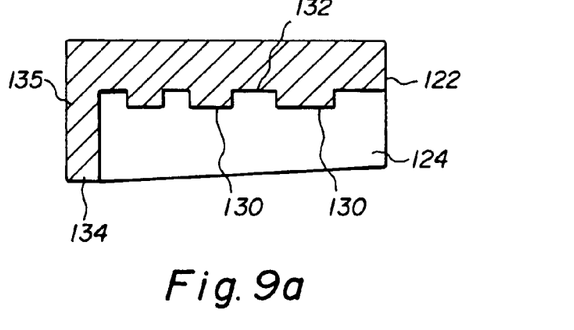
FIG. 9a is a slightly enlarged cross sectional view of a member of the compound bone device shown in FIG. 9 showing the end member.

Each bone member 122, 124 has been shaped to form a groove 131 on each longitudinally extending side of each member so that when the members are engaged as shown in FIG. 9, a composite groove 133 extends longitudinally the length of the compound bone device 120. The groove 133 is located on opposite sides of the compound bone device 120 and serves as a holding slot for the instrument which holds the compound bone device 120 while it is being machined. One end of each bone member 124 has been machined to provide an extended end member 134 which covers the end portion of bone member 122. The raised or extended end member 134 is flush with end surface 123 of member 122 and cooperate when members 122, 124 are mated together to form an impact surface 135 that can be struck with a hammer or other suitable instrument during a surgical procedure to implant the compound bone device 120 into a surgical site. A cross section of the bone member 124 showing end member 134 is shown in FIG. 9a.

The mating projections or teeth 130 range from 0.5 to 2.0 mm in height, preferably 11.0 mm and are formed by cutting a plurality of slots, grooves or channels 132 ranging from 1 to 4 mm in width with a generally rectangular shaped cross section in each mating surface 126, 128 of the bone tissue. The channels 132 are of equal dimensions and are preferably equally spaced about 2.0 mm to 2.12 mm apart. The channels 132 are preferably angled at +45 degrees and −45 degrees with respect to the longitudinally extending grooves 131.

The mating projections or teeth 130 formed by the channels 132 are comprised of a plurality of identical longitudinally spaced rectangular projections in a central portion of each mating surface 126, 128.

The mating projections 130 and the channels 132 on the bone members 122, 124 form complimentary inverse patterns that allow the members 122, 124 to be engaged or meshed together by press fitting the patterns together. This engagement prevents relative motion between the members 122, 124 in both the transverse and longitudinal directions to stabilize the compound bone device 120 during subsequent machining of the exterior surface of the device 120 and during or after implantation in a surgical site. The channels 132 are machined in the cortical bone to preferably a 1 mm depth and are angled at +45 degrees and −45 degrees in relation to edge 131 of each member 122, 124. The plus and minus 45 degree angles are the preferred angles for forming complimentary patterns on each surface 122, 124 because of ease of manufacturing, but any angle within a range of from about 15 degrees to about 75 degrees could be used in a similar way to cut other patterns forming mating surfaces 126, 128. It is understood that a degree of tolerance is necessary in the manufacturing process to assure that the members 122, 124 can be engaged and still provide sufficient structural support to the compound bone device 20. In all of the described embodiments, the maximum tolerance between the engaged parts at the surface ranges from 0.025 mm to 0.1 mm.

Two bores 122 and 143 respectively, extend through each bone member 122, 124. The bores 142, 143 are shown in phantom in FIG. 9. The bores 142, 143 are arranged so that when the members 122, 124 are engaged, the bores 142, 143 are axially aligned to form a continuous first bore 147 and a continuous second bore 149 through the compound bone device 120. Two cylindrical rods 346 and 350 such as those shown in FIGS. 8 and 8a are preferably made of cortical bone tissue and are press fit into each of the continuous bores 147, 149 to prevent the separation of the members 122, 124. Likewise the nail wedge 360 could be used to press or interference fit the two members together.

Figure 10:
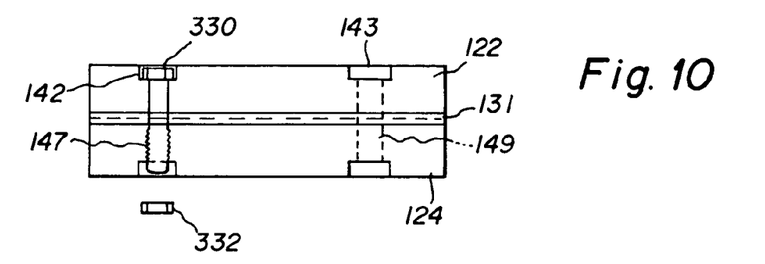
FIG. 10 is an assembled side elevational view of a compound bone structure with a countersunk bolt fastener member.

Thus, the mating surfaces 126, 128 of the bone members 122, 124 are secured together by at least one rod fastener member positioned at an oblique angle to the plane of the engaged mating surfaces as shown in FIGS. 1–7 and 9, 13 or normal to the plane of the engages mating surfaces as shown in FIGS. 10–12 and extending the full or partial thickness of the compound bone device 120. The wall forming each bore 147, 149 is cylindrical and each rod is cylindrical. Both rods 346 and 350 have a diameter slightly greater than the diameter of the bores 147, 149 so that the rods are retained in the bores by an interference fit and is constructed with a tolerance of 0.03 mm to 0.25 mm with respect to the bore diameter. If desired a suitable medical adhesive can be use to insure that the rods stay in the bores during insertion. It can be appreciated that the bores and rods can have other configurations as, for example, rectangular, triangular and the like such as nail wedge 360. Alternatively bolts 350, screws 342 and threaded rods 146 as shown in FIGS. 9, 10–12 can be screwed into threaded bores of the compound bone device. When the bone members 122, 124 are engaged and the rods are inserted to hold them together, an exterior surface of the compound bone device 120 can be shaped to form a suitable implant device for implantation into a surgical site. If desired, the exterior surface 48, 148, 248 can be scored or otherwise configured to present griping means which grips surrounding tissue when the compound bone device is implanted into the surgical site. The rods 146 provide sufficient structural reinforcement for the compound bone device to allow the device 120 to be machined to form the desired shape. Another compound bone device 220 is shaped so that when the device 220 is implanted in a surgical site, the anatomical load of the patient is applied in a direction that is normal to the engaged mating faces 226, 228. The normal direction is shown in FIG. 14 by an arrow N. It can be appreciated from the cross-section that when the two members 222, 224 are engaged, the projections on the first member 222 are disposed between or adjacent channels on the second member 224 to prevent the relative movement between the members 222, 224 in the longitudinal and transverse directions. There are some empty spaces between the mating faces 226, 228 of the compound bone device 220.

Figure 13:
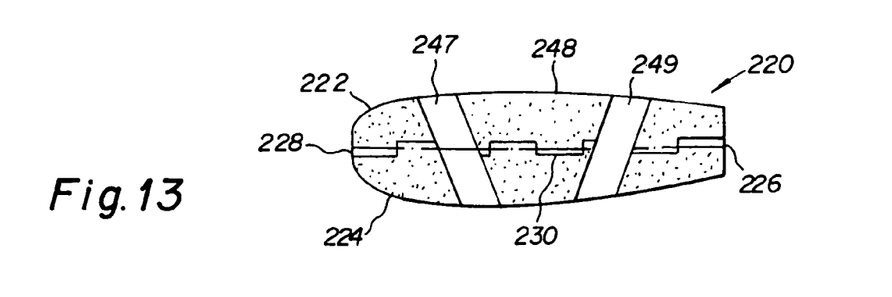
FIG. 13 is a cross sectional view of the compound bone structure.
Figure 14:
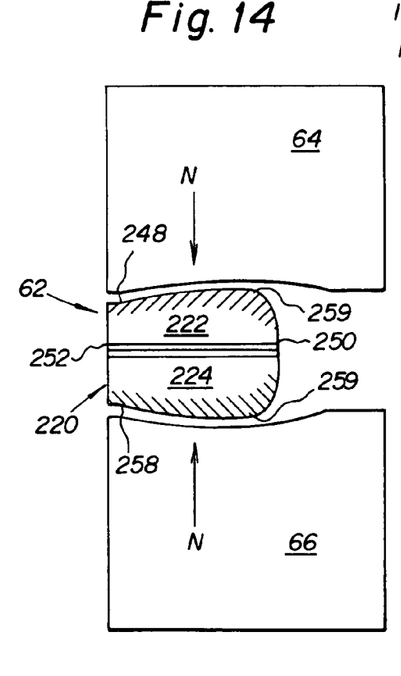
FIG. 14 is a schematic view of the compound bone device in a surgical site formed between an upper and a lower vertebrae in lumbar portion of a spine.

FIGS. 13 and 14 show that the exterior surface 248 of the compound bone device 220 can be shaped to form a intervertebral implant for the lumbar spine for insertion between vertebrae to fuse the vertebrae. The compound bone device 220 can be machined to provide a sloped and rounded proximal end 250 and distal end 252 for easy intervertebral insertion.

FIG. 13 shows a cross-section of a compound bone device 220 with the bores 247, 249 are angled with respect to the normal direction N. It can be appreciated that the normal direction is generally perpendicular to each of the engaged surfaces of the compound bone device 220. Each mating face 226, 228 is constructed and arranged to support a load that is applied in a direction that is normal to the surface. When the surfaces are engaged they can support an applied normal load and, because they are engaged, the normal load will not displace the bone members 222, 224 in the longitudinal or transverse directions relative to one another.

The bores 247, 249 generally form oblique angles with the engaged surfaces. It can be appreciated from FIG. 13 that the oblique angles of the bores 247, 249 are complimentary. That is, the angle of bore 247 is the inverse of or the negative of the angle of bore 249. The preferred angle of bore 247 with a line generally extending between the two faces is about 110 degrees and therefore the angle of bore 249 is negative 110 degrees. It should be noted that FIGS. 10–12 show transverse bores allowing the screw or bolt head or respective nut to lie planar in the countersink well.

FIG. 14 shows a schematic representation of the compound bone device 220 implanted in a surgical site 62 in the lumbar spine between an upper vertebra 64 and a lower vertebra 66 to fuse the vertebra. In this surgical procedure, an intervertebral space is enlarged and shaped to receive the allograft compound bone device 220 implant. The compound bone device 220 is inserted in the surgical site 62 so that the applied anatomical load N is applied in a direction that is normal or perpendicular to the engaged mating faces 226, 228.

The exterior surface 248 of the compound bone device 220 is shaped to support the applied load in a direction that is normal to the engaged faces 226, 228 and to maintain the orientation of the implanted compound bone device 220 in the surgical site 62 throughout the post-operative period.

The engaged faces 26, 28, 126, 128, and 226, 228 support the major anatomical load of the patient during the post operative recovery period. The engagement between the respective projections 30, 130, and 230 on the two mating faces 26, 28, 126, 128, and 226, 228 assure that the first and second bone members 22, 24, 122, 124, and 222, 224 do not move relative to one another in the longitudinal or transverse directions during the post operative period.

It is desired that the compound bone devices 20, 120, and 220 hold together during the post operative period to allow resorption and remodeling to occur in the allograft tissue and rods are used to hold the same together. The fastening rods 46, 146 (rods 246 not shown), 346 and 350 which are inserted in bores 47; 147, 149, and 247, 249 can be made of cortical, allograft tissue. The outer surface of each cortical rod is entirely within and surrounded by the bone mass of the compound bone device so that the rod is substantially protected from the biochemical attack that occurs from normal biological and biochemical processes as the implant is integrated into the bone of the patient. Only the end surfaces of the rods 46, 146, 346 and 350 are exposed, but this results in minimal structural degradation of each rod.

The biological and biochemical process cause a slow absorption of the implanted bone to occur over time. This absorption could structurally degrade the interlocking bone members of the compound bone device. Because the anatomical load is normal to the mating complimentary surfaces, the anatomical load can be sustained even during tissue degradation. Because the rods are substantially protected from the biochemical mechanism of absorption, the rods will continue to secure the bone members together long enough to allow full healing and integration to occur. The cortical rods 46, 146, 348 and 360 are embedded and held tightly in the mass of the implant and are protected from the biochemical attack of the patient except at the two end surfaces of each rod. The rods remain structurally intact during the post-operative period to help maintain the structural stability of the compound bone device 20, 120, and 220.

The normal absorption mechanisms that occur during the healing process also tend to structurally degrade the two engaged bone members of the compound bone device 20, 120 and 220 during the post operative period. Because the anatomical load is normal to the engaged surfaces, the applied load can be supported by the device 20, 120, and 220 even though some degradation of the allograft tissue does occur. Because the length of the interlocking rods are protected from biochemical degradation, the rods continues to secure and hold the two bone members 22, 24; 122, 124; and 222, 224 in place long enough for full resorption and remodeling to occur. The cortical tissue of the compound bone device 20, 120, and 220 has been observed to last 6 to 12 months before being fully integrated into the host patient.

The assembled compound bone device 220 shown in the schematic view in FIG. 14 was tested in a cadaver lab in which it was inserted into the lumbar spine. The procedure requires that the assembly be hammered using considerable force into the intervertebral disc space. Four compound bone devices were successfully inserted into the spine with no signs of impact damage due to the insertion.

It can be understood by one skilled in the art that the preferred embodiment described above is intended as an example only to teach the broad principles of the invention and is not intended to be limiting. It can be understood, for example, that the mating projections or teeth 30, 130, 230 are constructed and arranged so that when the two mating faces 26, 28 and 126, 128 and 226, 228 are engaged, there is no significant relative movement between the bone members in the longitudinal and transverse directions outside of that permitted by the manufacturing tolerances and by any structural changes that occur in the bone device during the post operative period.

It is appreciated that many geometric configurations of projections on each mating face can provide suitable structures to prevent relative movement between the bone members in the longitudinal and transverse directions.

Figure 15:
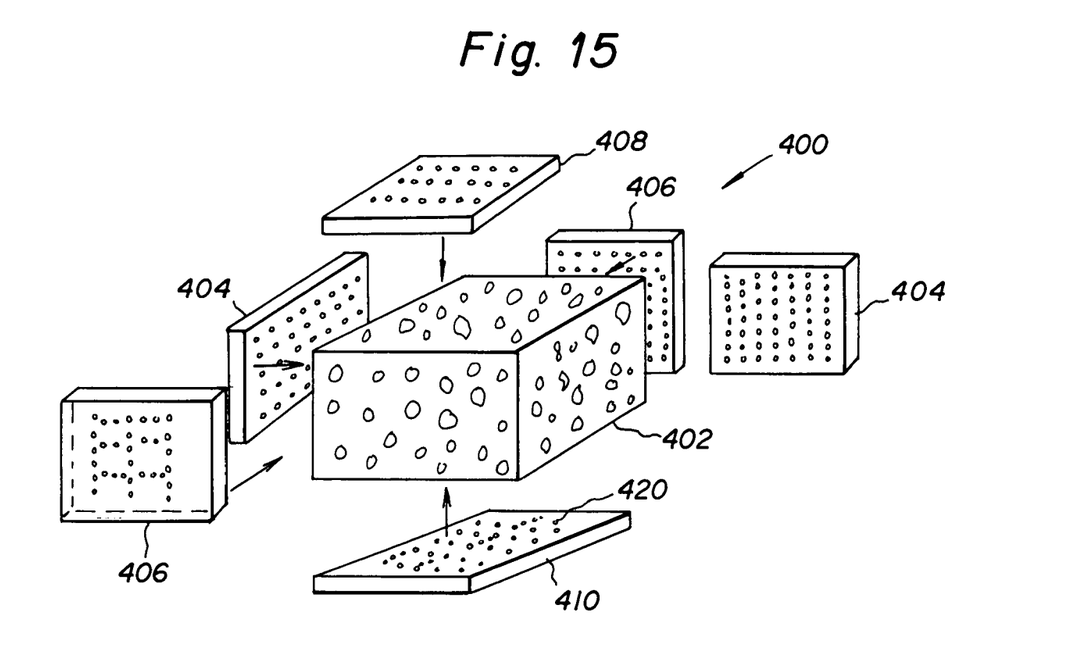
FIG. 15 is an exploded view of the composite cortical/cancellous compound bone embodiment.

In another embodiment of the invention as shown in FIG. 15 a composite bone assembly 400 is constructed of a center cancellous base block 402, side plates 404, end plates 406 and a top plate 408 and bottom plate 410. All of the plates are constructed of cortical bone and the six plate sides are fastened to the central block 402 by adhesives, rods, screws or other suitable fasteners. The plates are drilled with throughgoing holes 420 to allow body fluids access to the base block 402 to facilitate bone growth. While the center block is shown to be rectangular in shape, a wedge shape or other shape could be substituted.

Figure 16:
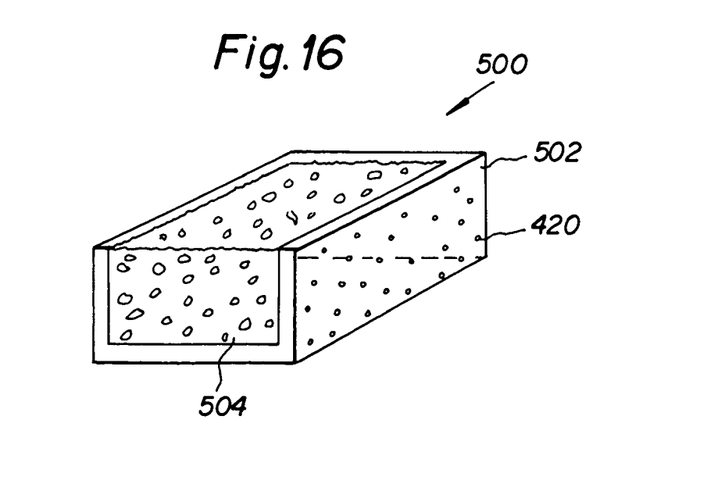
FIG. 16 is an exploded view of another composite cortical/cancellous compound bond embodiment.

In an alternate embodiment of the composite bone assembly invention as shown in FIG. 16 a composite bone assembly 500 is constructed of a U shaped cortical base 502 which holds a cancellous block 504 therein by interference fit, adhesives, threaded fasteners or press fit fasteners. The open surface of the cancellous material speeds up bone formation.

In general, a plurality of mating projections and channels forming mating spaces are provided on a first mating face and a plurality of mating projections and mating spaces are provided on a second mating face. When the faces are engaged or mated, the mating teeth on the first face are disposed within the mating spaces on the second mating face and the mating teeth on the second mating face are disposed within the mating spaces on the first mating face to prevent the relative movement between the bone members in the longitudinal and transverse directions when the bone members are inserted into a surgical site or are disposed in a surgical site during a post operative period. Each mating face is constructed and arranged to support an applied load applied in a normal direction and to engage a mating face with complimentary projection receiving construction.

All of the compound bone devices described above allow for constructions 10 mm×25 mm or larger. This assembly technique considerably broadens the use of allograft tissues by allowing much larger implants to be formed than could have been attained from the normal human anatomy.

It can also be understood that because the preferred embodiment is illustrative only, as it is contemplated to provide a compound bone device comprised of more than two bone members. In such a case, the compound bone device can be thought of as being comprised of an upper member, a middle member(s) and a lower member. The upper and lower members are provided with a single mating face and the middle member(s) is provided with two mating faces generally disposed on opposite sides thereof so that the three or more bone members or pieces can be engaged and fastened together with at least one embedded cortical bone rod, preferably located at an oblique angle to the longitudinal plane of the mating surfaces. In this regard the composite block member 400 can be provided with stacked plates to form the respective walls.

Because bones are irregularly shaped and because not all applications of the invention require that the implant support an anatomical load that is applied in generally one direction, it can be understood that if more than one pair of engaged mating faces is present in a single compound bone device, the pairs need not necessarily be parallel nor do the individual members of each pair have to be generally planar to form a compound bone device.

The compound bone device can be constructed and arranged to support a load applied in a direction that is generally normal to the two pairs of engaged faces so that the bone device can support an anatomical load and prevent the relative displacement of the three bone pieces in a longitudinal or transverse direction.

It can further be understood that because the illustrated embodiment is exemplary only, it is contemplated to provide compound bone devices which are shaped for many applications and that the compound bone device design is not restricted to use in the lumbar spine for spinal fusion. A compound bone device comprised of two or more bone members can be shaped during the manufacturing process to form compound bone rods, bone screws, plates, discs, wedges, blocks and other devices of various configurations.

The compound bone device can be fabricated from xenograft, autograft or allograft bone tissue and it is contemplated to use any suitable bone tissue from any source to form a compound bone device.

It is also understood that although it is preferred to fabricate the compound bone device without the use of adhesives or synthetic absorbable or nonabsorbable polymers or metals, it is within the scope of the invention to additionally secure together the bone members with any suitable surgical bone adhesive or with a synthetic absorbable or nonabsorbable polymer or in any combination with or without at least one component made of bone tissue.

In the foregoing description, the invention has been described with reference to a particular preferred embodiment, although it is to be understood that specific details as shown are merely illustrative, and the invention may be carried out in other ways without departing from the true spirit and scope of the following claims.

We claim:

1. A compound bone device made from sterile bone tissue for implantation into a surgical site which supports an anatomical load applied to the compound bone device during a post-operative period while the implanted bone tissue is being resorbed and remodeled, comprising:
    a first bone member defining a first mating face constructed and arranged to support a load in a direction that is normal to the first mating face and to receive and engage a complimentary mating face of a second bone member;
    a second bone member defining a second mating face that is complimentary to the first mating face of the first bone member constricted and arranged to support a load in the direction normal to the second mating face, said mating faces being mounted to each other so that the first and second bone members form a compound bone device which prevents displacement of the first bone member with respect to the second bone member in both a longitudinal direction and a transverse direction when an anatomical load is applied;
    each bone member defining a bore within its body which is angularly oriented with respect to a plane across its mating face and opens on said mating face, each bore being axially aligned with an angularly oriented bore defined in the body of the other bone member and a wedge nail with an angular cross section press fit in said axially aligned bores and extending across said mating face in an interference fit to hold the first and second bone members in engagement resisting separation of the first and second bone members.

* * * * *